United States Patent [19]

Kunz et al.

[11] 4,224,249

[45] Sep. 23, 1980

[54] TOLUENE DIAMINE FROM NON-WASHED DINITROTOLUENE

[75] Inventors: Nance D. Kunz, Bethlehem; Thomas A. Johnson, Orefield; Barton Milligan, Coplay, all of Pa.

[73] Assignee: Air Products and Chemicals, Inc., Allentown, Pa.

[21] Appl. No.: 38,976

[22] Filed: May 14, 1979

[51] Int. Cl.$^2$ .................. C07C 85/11; C07C 85/26
[52] U.S. Cl. ............................ 260/580; 260/582; 260/689; 260/705
[58] Field of Search .......................... 260/580, 582

[56] References Cited

U.S. PATENT DOCUMENTS 3,546,296  12/1970  Gobron et al. .................. 260/580

Primary Examiner—John Doll

Attorney, Agent, or Firm—Russell L. Brewer; E. Eugene Innis

[57] ABSTRACT

This invention relates to an improvement in a process for preparing toluene diamine. The improvement resides in a process which is capable of permitting reduction of dinitrotoluene to toluene diamine without prior alkaline treatment for removal of nitrocresols in the dinitrotoluene. In carrying out the improvement the feed dinitrotoluene is water washed to remove $HNO_3$ to a level below 6000 ppm, and the catalytic conversion of dinitrotoluene to toluene diamine is done continuously. Dinitrotoluene is charged to a reaction vessel containing a liquid carrier and reduced with hydrogen at constant pressure, the dinitrotoluene being added at a rate to maintain a concentration of dinitrotoluene of 0.0001 to 25% by weight of the total reactor contents while the hydrogenation catalyst is maintained at a level from about 0.1 to 3% based on the weight of reactor contents.

5 Claims, No Drawings

TOLUENE DIAMINE FROM NON-WASHED DINITROTOLUENE

BACKGROUND OF THE INVENTION

1. Field of the Invention

This invention relates to a process for producing toluene diamine from an impure dinitrotoluene reactant.

2. Description of the Prior Art

U.S. Pat. No. 2,131,734 is typical of the early processes for the liquid phase hydrogenation of dinitrotoluene to toluene diamine. Typically, the hydrogenation was carried out in the presence of nickel supported on a silica substrate and in the presence of a small amount of an alkaline substance such as caustic soda. Typical amounts of catalysts were 0.5–2% catalyst metal by weight of the dinitrotoluene. Temperatures were from 80° to 140° C. and pressures were from 200 to 500 pounds per square inch.

U.S. Pat. No. 2,976,320 represented an improvement over the early liquid phase hydrogenation processes of dinitrotoluene. In that process, the temperature of reaction was reduced to less than 100° C. to prevent hazards due to the instability of the dinitrotoluene. Low temperature hydrogenation was accomplished by first reducing the nitrocresol content in the feed and then using a palladium or platinum catalyst to effect hydrogenation. It was reported that nitrophenols or nitrocresols, which are normally present in commercial dinitrotoluenes, are catalyst poisons and decomposition accelerators, and that by limiting the concentration to less than 500 ppm, and preferably 200 ppm, a dinitrotoluene could be hydrogenated safely at low temperatures. One of the typical ways of removing the nitrocresols and nitrophenols was by washing the crude dinitro product, obtained by separation from the spent nitration acid, with dilute aqueous alkali (e.g., sodium carbonate solution). The product then was water washed.

U.S. Pat. No. 3,093,685 discloses a liquid phase process for reducing dinitrotoluene to toluene diamine with the improvement residing in carrying out the reduction in the presence of water of reaction with no other solvent or diluent being added.

U.S. Pat. No. 3,356,728 differs from the patents previously cited in that it relates to a continuous process for reducing dinitrotoluene to toluene diamine. It was disclosed that various operating problems such as poor catalyst life and operating hazards due to the instability of the dinitrotoluene could be minimized by using the continuous process wherein the catalyst was present in about 2 to 25% by weight of the slurry with extremely low concentrations of dinitrotoluene as the reactant. The level of nitro compound was maintained at 0.15 pound equivalents nitro groups per pound of catalyst. Temperatures of 100°–140° C. and pressures of 100–2000 psig, preferably 200–500 psig hydrogen were used. Raney nickel catalyst was used in the hydrogenation procedure.

U.S. Pat. No. 3,546,296 relates to another continuous process for producing toluene diamine by the reduction of dinitrotoluene utilizing specific reactor equipment. Again, the concentration of dinitrotoluene in terms of the catalyst is extremely low so as to reduce operating hazard.

SUMMARY OF THE INVENTION

This invention relates to an improvement in a continuous process for preparing toluene diamine by the catalytic hydrogenation of dinitrotoluene. The improvement resides in the ability to utilize a crude dinitrotoluene feedstock prepared by the mixed $H_2SO_4/HNO_3$ acid nitration of toluene which has not been subjected to alkaline treatment as a reactant. The improvement in the basic process of preparing toluene diamine by reacting non-alkaline treated crude dinitrotoluene feedstock with hydrogen in the presence of a hydrogenation catalyst comprises:

(a) water washing the crude feedstock to reduce the acid concentration in the feedstock to less than 6,000 ppm, if above;

(b) continuously introducing dinitrotoluene and hydrogen to a reactor vessel, (c) maintaining a concentration of dinitrotoluene from about 0.0001 to 25% by weight;

(d) maintaining a hydrogenation catalyst concentration of about 0.1 to 20% by weight of liquid reaction mass; and (e) utilizing a hydrogenation catalyst containing a metal selected from the group consisting of nickel, cobalt, chromium and iron.

Several advantages are associated with the improvement of this invention, and these advantages include:

an ability to hydrogenate dinitrotoluene without prior alkaline treatment for reducing alleged catalyst poisoning nitrocresols and nitrophenols;

an ability to eliminate alkaline treatment of dinitrotoluene without adversely effecting hydrogenation conditions, thus saving on the expense of chemicals;

an ability to reduce the problems associated with environmental disposal of nitrocresol and nitrophenol salts as associated with the prior art by virtue of the elimination of the alkaline treatment; and an ability to hydrogenate non-alkaline washed dinitrotoluene without noticeable loss of catalyst life or product, toluene diamine purity.

DESCRIPTION OF THE PREFERRED EMBODIMENTS

Dinitrotoluene which is used as a reactant in the present process is produced conventionally by nitrating toluene using the mixed acid technique. In this process, the toluene is reacted with a mixture of nitric acid, sulfuric acid, and water under conditions effective for producing dinitrotoluene. Conventionally, the crude dinitrotoluene is removed from the reactor, passed into a phase separator and the product separated from the aqueous acid phase. Further purification of the crude product is effected by washing with water to remove contaminant acid material followed by treatment with an alkali, e.g. sodium carbonate to reduce the level of nitrocresols and nitrophenols (nitrophenolic material) in the dinitrotoluene product. As noted in the prior art, the primary purpose of the alkaline treatment was to remove the nitrocresols and nitrophenols as these components were believed to reduce catalyst life during the reduction of the dinitrotoluene to toluene diamine.

The process of this invention can tolerate crude dinitrotoluene which has not been treated with alkaline material as a reactant and even permit concentrations of nitrocresols and nitrophenols to at least a level of 1200 parts per million (ppm). Under the batch processes, these concentrations of nitrocresols and nitrophenols could not be tolerated as evidenced by U.S. Pat. No. 2,976,320. Although not intending to be bound by theory, it is speculated that the batch hydrogenation process was not sensitive to nitrocresols and nitrophenols as reported but rather was sensitive to acid. This belief is based on information from the continuous process of this invention which shows an acid concentration of above 6,000 ppm seriously diminishes catalyst life and increases tar while the reaction appears relatively insensitive to nitrophenolic material. In the prior art the alkaline treatment not only removed both nitrocresols and nitrophenols but also the acid, and apparently based on the improved results obtained it was perhaps wrongly concluded that catalyst life was sensitive to nitrocresols, etc. rather than acid. Based on experimental data water washing of the contaminated dinitrotoluene is all that is necessary in the continuous process if the acid concentration is above 6,000 ppm. Water washing is usually conducted so the acid level is 2,500 ppm or below.

The temperatures and pressures utilized in the process remain unchanged from the prior art and, for example, such temperatures are generally from about 50° to 200° C. but preferably at a temperature of from about 90° to 130° C. Hydrogen pressures of 25–2000 psig can be utilized, but generally the pressures are from about 100–250 psig.

The hydrogenation of dinitrotoluene is carried out in the presence of a hydrogenation catalyst. Any of the various non-precious metal catalysts which have been disclosed in the prior art promoting this reaction may be employed. These catalysts may be pelleted, granular, or powdered, although the powdered form having a particle size of from 1–350 microns is preferred. Metals that can be used for forming the catalyst are nickel, nickel promoted by cobalt, chromium, molybdenum and iron. Raney nickel type catalysts are the preferred catalysts since in the continuous process they are relatively insensitive to nitrophenolic material. The hydrogenation catalyst metals may be present on a support such as kieselguhr, silica, silica-alumina, and alumina although in the preferred case the Raney nickel type catalysts are unsupported.

The proportion of hydrogenation catalyst utilized in the reaction is quite low, e.g. from about 0.10 to 20% preferably from about 0.1 to 3%. When the concentration of catalyst exceeds about 2% by weight little improvement is realized. When the catalyst level falls below about 0.1% by weight there is insufficient catalyst to effect rapid hydrogenation of the dinitrotoluene and long residence times are required.

The proportion of dinitrotoluene is maintained in a proportion of 0.0001 to 25% by weight of the reaction mixture. Preferred results utilize a concentration of 0.01–3%.

The following examples are provided to illustrate the invention and all the parts and percentages are by weight unless otherwise specified.

EXAMPLE 1

The hydrogenation of dinitrotoluene was conducted in several runs to determine the effectiveness of the process. The reactor used was a stirred one liter Parr 316 stainless steel autoclave. The dinitrotoluene was charged to the autoclave on a semi-continuous (pulse) basis with the product being removed from the autoclave in corresponding intermittent relationships so that a constant volume of 500 milliliters was maintained in the autoclave. The crude dinitrotoluene fed to the reactor had the following general analysis and was obtained from a commercial production unit after it had been washed with water (WW DNT) but not being exposed to sodium carbonate treatment. The control was both water washed and carbonate treated.

| Dinitrotoluene | 99.0% |
|---|---|
| Nitrophenolic material | 0.080% |
| Nitric Acid | 1200 ppm |
| Balance | approximately 1% |

First the autoclave was charged with 500 ml of a mixture of 60% toluene diamine and 40% water by weight containing about 0.4% by weight pyrophoric Raney nickel catalyst having a particle size of from 1 to 350 microns. Then the contents were heated in the autoclave to a temperature of 130° C. and then the autoclave was pressurized with hydrogen. Although the operation was a semi-batch mode because of intermittent feed and intermittent removal of product the operation was deemed continuous because the autoclave remained at substantially constant volume and the pulse rate was relatively rapid. The dinitrotoluene was fed to the reactor at a rate of 1.45 gms/minute which translates to turnover numbers of 43.6 parts DNT reduced per hour per part catalyst and a maximum concentration of about 0.3% DNT. The average reaction time allowed for the dinitrotoluene was about 1–1.5 minutes even though the reduction takes place almost instantly.

Table 1 represents two runs, one as a control wherein the dinitrotoluene had been exposed to sodium carbonate treatment with the result that practically no nitrophenolic material or acid was present (control) and the other using the feed above wherein the nitrophenolic material had not been removed but only the residual acid due to water washing (WWDNT). Results are as follows in Table 1. Catalyst concentration, pressures and other variables are given.

TABLE 1

|  | Run #1 Control | Run #2 WW DNT |
|---|---|---|
| Temperature (°C.) | 130 | 130 |
| Pressure (psig) | 160 | 160 |
| Catalyst Conc. (wt. %) | .4$^{(a)}$ | .4$^{(a)}$ |
| Operating mode | incremental feed$^{(b)}$ | incremental feed$^{(b)}$ |
| Vapor phase H$_2$ Concentration (%) | 100 | 100 |
| Catalyst Feed Mode | batch | batch |
| Initial Activity $\frac{\text{gmol H}_2}{(\text{min}) (\text{gm cat}) (\text{cm}^3)}$ | $1.37 \times 10^{-4}$ | $9.34 \times 10^{-5}$ |
| Tar generation (%)$^{(f)}$ | 0.2–1.3% | 0.1–2% |
| Turnover $\frac{\text{part DNT}}{\text{hr. part cat.}}$ | 43.62 | 43.62 |
| Catalyst life $\frac{\text{part DNT}}{\text{part cat}}$ | 1975 | 1885 (minimum)$^{(c)}$ |

TABLE 1-continued

|  | Run #1 Control | Run #2 WW DNT |
|---|---|---|
| Deactivation rate | $-.0086\% \frac{\text{initial rate}}{\text{gm DNT reduced}}$ | $-.0091\% \frac{\text{initial rate}}{\text{gm DNT reduced}}$ |
| Material balance closure (%) | 94.7 | 97.1 |

[a] 2 gms of catalyst in 500 gm reaction mass
[b] With pulse-in, pulse out systems autoclave liquid volume was maintained at 500 ml.
[c] Experiment terminated at this point; exhausted dinitrotoluene feed stock.

The results show that water washed dinitrotoluene could be hydrogenated without an adverse effect on catalyst life or rate of reaction. The catalyst performance in Run 2 was substantially the same as Run 1 and it was lower only because of an exhausted feedstock. Tar generation was slightly higher in Run 2. This value may not represent any greater loss of material since tar generation in Run 1 does not include the nitrophenolic material removed by alkali treatment.

EXAMPLE 2

The procedure of Example 1 was repeated except that different feed and higher catalyst concentrations were used. The feed analyzed as follows for the alkaline treated dinitrotoluene feed and the water washed dinitrotoluene feed.

TABLE 2

|  | Run #3 Control | Run #4 WW DNT |
|---|---|---|
| Temperature (°C.) | 130 | 130 |
| Pressure (psig) | 160 | 160 |
| Catalyst Conc. (wt. %) | 1.7[a] | 1.7[a] |
| Operating mode | incremental feed[b] | incremental feed[b] |
| Vapor phase |  |  |
| H₂ Concentration (%) | 100 | 100 |
| Catalyst Feed Mode | batch | batch |
| Initial Activity $\frac{\text{gmol H}_2}{\text{(min) (gm cat) (cm}^3\text{)}}$ | 3.67 × 10⁻⁵ | 3.67 × 10⁻⁵ |
| Tar generation (%)[f] | .41-1.28% | .48-1.75% |
| Turnover $\frac{\text{part DNT}}{\text{hr. part cat.}}$ | 21.03 | 21.03 |
| Material balance closure (%) | 95.5 | 96.8 |

[a] 8.5 grams catalyst in 500 gm. reaction mass
[b] With pulse-in, pulse-out systems autoclave liquid volume was maintained at 500 ml.

| FEED Compositions |  |  |
|---|---|---|
| Analysis/Sample | Run #3 Control DNT Feed | Run #4 WW DNT Feed |
| Water (ppm) | 4400 | 4800 ± 100 |
| Freezing pt. (°C.) | 56.2 ± .1 | 57.1 ± 0.1 |
| Acidity (ppm as H₂SO₄) | 1 | 3000 ± 200 |
| Alkalinity (ppm as KOH) | Nil | Nil |
| Cresols (ppm) | 8 ± 1 | 700 ± 10 |
| 2,4,6 TNT (ppm) | 730 ± 40 | 1100 ± 30 |
| nitrobenzene (wt. %) | 0.01 | 0.02 |
| o-nitrotoluene (wt. %) | 0.02 | 0.01 |
| m-nitrotoluene (wt. %) | 0.01 | 0.01 |
| p-nitrotoluene (wt. %) | 0.02 | 0.01 |
| 2,6 Dinitrotoluene (wt. %) | 19.14 | 17.73 |
| 2,5 Dinitrotoluene (wt. %) | 0.75 | 0.68 |
| 2,4 Dinitrotoluene (wt. %) | 75.44 | 77.17 |
| 3,5 Dinitrotoluene (wt. %) | 0.03 | 0.03 |
| 2,3 Dinitrotoluene (wt. %) | 1.62 | 1.47 |
| 3,4 Dinitrotoluene (wt. %) | 2.46 | 2.23 |
| Normalized isomer ratio 2,4/2,6 | 79.7/20.2 | 81.3/18.7 |
| Nitrate (ppm) | 0.3 | 1092 ± 20 |
| Nitrite (ppm) | 0.35 ± .07 | 160 ± 8 |
| Sulfate (ppm) | 0.69 ± 0.26 | 230 ± 50 |

| -continued |  |  |
|---|---|---|
| FEED Compositions |  |  |
| Analysis/Sample | Run #3 Control DNT Feed | Run #4 WW DNT Feed |
| Oxalate (ppm) | 0.2 | 170 ± 44 |
| Acetate (ppm) | 2.47 ± 0.4 | — |

The results are given in Table 2.

The results in terms of catalyst activity and reaction rate for both the control and the water washed dinitrotoluene appeared to be similar. Slightly higher tar generation with the water washed dinitrotoluene was noted. It is also noted the reaction is relatively insensitive to nitrophenolic material as the concentration was about 700 ppm. Table 3 below represents analysis of the percentage tar versus the grams of dinitrotoluene reduced per gram of catalyst.

TABLE 3

| Tar Analyses (wt. %) |  |  |  |  |  |
|---|---|---|---|---|---|
|  |  | Run #3 Control |  | Run #4 WW DNT |  |
| Gms. DNT Reduced Per Gm. Catalyst | % Reaction Mass Produced From Feed | % Tar | DNT (ppm) | % Tar | DNT (ppm) |
| 0 | 0 | 0.412 | 5.0 | 0.482 | 5.0 |
| 59.5 | 51.9 | 1.02 | 5.0 | 0.888 | 5.0 |
| 116.8 | 76.4 | 1.28 | 5.0 | 0.99 | 5.0 |
| 175.3 | 88.6 | 1.108 | 5.0 | 1.30 | 5.0 |
| 233.2 | 94.4 | 1.27 | 5.0 | 1.54 | 5.0 |
| 289.1 | 97.24 | 0.904 | 5.0 | 1.66 | 5.0 |
| 300.2 | 97.7 | 1.28 | 5.0 | 1.75 | 5.0 |

Table 3 shows that the tar concentration is slightly higher for the water washed dinitrotoluene feedstock particularly at higher levels of dinitrotoluene reduced per gram of catalyst. Even so the percent tar produced is relatively insignificant in terms of the benefit gained, i.e. the ability to eliminate the alkaline treatment of dinitrotoluene and associated high chemical cost. Also, the process eliminates the environmental problems associated with the alkaline treatment.

EXAMPLE 3

The procedure of Example 1 was repeated in order to determine the sensitivity of the process to acid concentration. The DNT feedstock used was product DNT (control) spiked with nitric acid to an acid concentration of 10,000 ppm. The 10,000 ppm level was used as it approximates the acid concentration of crude DNT prior to water washing. In carrying out the test the spiked DNT was continuously added to a reactor containing 40% H₂O and 60% toluene diamine. During the addition the acid concentration was monitored. The hydrogenation was compared with water washed DNT.

The results are in Table 4.

TABLE 4

|  | WW DNT | Product DNT with 10,000 ppm HNO$_3$ |
|---|---|---|
| Initial Activity (mol H$_2$/ min. g cat. cm$^3$) | 3.67 × 10$^{-5}$ | 6.0 × 10$^{-5}$ |
| Final Activity (mol H$_2$/ min. g cat. cm$^3$) | 3.67 × 10$^{-5}$ | 2.03 × 10$^{-5}$ |
| Tar Generation (Wt. %) | 1.7 | 4 at 6000 ppm HNO$_3$ 10–30 above 6000 ppm HNO$_3$ |
| Catalyst Life gm DNT/gm cat. | 1800 | 220 |
| Nitrobody in reactor (ppm) | 5 | 5 below 6000 ppm HNO$_3$ 5500 above 6000 ppm HNO$_3$ |

Final catalyst activity of the product DNT corrected for difference in volume to the activity of the WW DNT was $1.24 \times 10^{-5 (mole\ H_2/min\ gm\ cat\ cm)}$. At 6000 ppm HNO$_3$, based on feed concentration, the catalyst activity had diminished by about ⅔, and shortly after the catalyst completely failed.

What is claimed is:

1. In a process for preparing toluene diamine which comprises reacting dinitrotoluene with hydrogen in the presence of a hydrogenation catalyst, the improvement for permitting reaction of the crude dinitrotoluene feedstock without alkaline treatment with hydrogen which comprises:
   (a) water washing the crude feedstock to reduce the acid concentration in the feedstock to less than 6000 ppm;
   (b) continuously introducing dinitrotoluene and hydrogen to a reaction vessel;
   (c) maintaining the concentration of dinitrotoluene in a range from about 0.0001 to 25% by weight;
   (d) maintaining a hydrogenation catalyst concentration of from about 0.1 to 20% based on the weight of reactor contents; and
   (e) utilizing a hydrogenation catalyst containing a metal selected from a group consisting of molybdenum, nickel, cobalt, chromium, iron and mixtures thereof.

2. The process of claim 1 wherein said dinitrotoluene concentration maintained in the reactor is from 0.01 to 3% by weight.

3. The process of claim 2 wherein said catalyst level is maintained from 0.1 to 3%.

4. The process of claim 3 wherein said metal catalyst is Raney nickel.

5. The process of claim 4 wherein the crude dinitrotoluene feedstock is water washed to the extent that the acid concentration is not above 2500 ppm.

* * * * *